United States Patent
McElroy et al.

(10) Patent No.: US 10,673,555 B2
(45) Date of Patent: Jun. 2, 2020

(54) SECURE CHANNEL SOUNDING

(71) Applicant: Decawave, Ltd., Dublin (IE)

(72) Inventors: Ciaran McElroy, Dublin (IE);
Jaroslaw Niewczas, Jozefow (PL);
Michael McLaughlin, Dublin (IE);
Igor Dotlic, Dublin (IE); Marcas O'Duinn, Dublin (IE); Dries Neirynck, Chelmsford (GB)

(73) Assignee: DecaWave, Ltd., Dublin (IE)

( * ) Notice: Subject to any disclaimer, the term of this patent is extended or adjusted under 35 U.S.C. 154(b) by 0 days.

(21) Appl. No.: 16/042,727

(22) Filed: Jul. 23, 2018

(65) Prior Publication Data

US 2020/0028607 A1   Jan. 23, 2020

(51) Int. Cl.
| | |
|---|---|
| *A61M 25/01* | (2006.01) |
| *H04J 13/00* | (2011.01) |
| *H04J 13/10* | (2011.01) |
| *H04B 1/717* | (2011.01) |

(52) U.S. Cl.
CPC ........ *H04J 13/0014* (2013.01); *H04B 1/7174* (2013.01); *H04J 13/0025* (2013.01); *H04J 13/10* (2013.01); *A61M 2025/0166* (2013.01)

(58) Field of Classification Search
USPC .......................................................... 370/329
See application file for complete search history.

(56) References Cited

U.S. PATENT DOCUMENTS

| | | | | |
|---|---|---|---|---|
| 9,645,228 | B1 * | 5/2017 | Doerry ................. | G01S 13/284 |
| 2007/0036353 | A1 * | 2/2007 | Reznik ................ | H04B 7/0434 |
| | | | | 380/30 |
| 2008/0013602 | A1 | 1/2008 | McLaughlin | |
| 2013/0039285 | A1 * | 2/2013 | Sorrentino ............ | H04L 5/0091 |
| | | | | 370/329 |
| 2014/0258575 | A1 * | 9/2014 | Su ........................ | G06F 13/362 |
| | | | | 710/110 |
| 2017/0064546 | A1 * | 3/2017 | Baligh .................. | H04W 12/04 |

FOREIGN PATENT DOCUMENTS

WO        2004038988 A2     5/2004

OTHER PUBLICATIONS

Muhammad S Sohail, et al: "A non-iterative channel estimation and equalization method for TDS-OFDM systems", Wireless Communications and Mobile Computing Conference (IWCMC), 2011 7th International, IEE, Jul. 4, 2011, pp. 1418-1422, XP031962181, DOI: 10.1109/IWCMC.2011.5982746, ISBN: 978-1-4244-9539-9 abstract section 1) Channel Estimation in Time Domain; p. 1418—right-hand column.

* cited by examiner

*Primary Examiner* — Eva Y Puente
(74) *Attorney, Agent, or Firm* — Hunt Pennington Kumar & Dula PLLC

(57) ABSTRACT

In an ultra-wideband ("UWB") communication system comprising a pair of UWB transceivers, methods for securely performing channel sounding. In a first GCP Sync method, a pre-determined set of Golay Complementary Pairs is added to an 802.15.4a frame. In a second CLASS method, a cyphered low auto-correlation sum set is added to frame. In a third LCSSS method, a low cross-correlation sidelobe sum set is added to the frame. In general, these methods are adapted to transmit a pseudo-randomly generated codeset which may have inherent sidelobe distortions, and then, in the receiver, to compensate for this, and any channel-induced, distortion by selectively modifying the cross-correlation codeset.

16 Claims, 12 Drawing Sheets

SECURE CHANNEL SOUNDING

CROSS-REFERENCE TO RELATED APPLICATIONS

This application is related to the following:
1. Provisional Application Ser. No. 62/291,407, filed 4 Feb. 2016 ("First Parent Provisional");
2. Provisional Application Ser. No. 62/291,605, filed 5 Feb. 2016 ("Second Parent Provisional");
3. Provisional Application Ser. No, 62/300,781, filed 27 Feb. 2016 ("Third Parent Provisional");
4. Provisional Application Ser. No. 62/370,440, filed 3 Aug. 2016 ("Fourth Parent Provisional");
5. Provisional Application Ser. No. 62/375,788, filed 16 Aug. 2016 ("Fifth Parent Provisional"); and
6. Provisional Application Ser. No. 62/379,168, filed 24 Aug. 2016 ("Sixth Parent Provisional");

This application claims priority to the First, Second, Third, Fourth, Fifth and Sixth Parent Provisionals, and hereby claims benefit of the filing dates thereof pursuant to 37 CFR § 1.78(a)(4).

The subject matter of the First, Second, Third, Fourth, Fifth and Sixth Parent Provisionals, each in its entirety, is expressly incorporated herein by reference.

BACKGROUND OF THE INVENTION

1. Field of the Invention

The present invention relates generally to wireless communication systems, and, in particular, to a wireless communication system adapted securely to perform channel sounding.

2. Description of the Related Art

In general, in the descriptions that follow, we will italicize the first occurrence of each special term of art which should be familiar to those skilled in the art of ultra-wideband ("MB") communication systems. In addition, when we first introduce a term that we believe to be new or that we will use in a context that we believe to be new, we will hold the term and provide the definition that we intend to apply to that term. In addition, throughout this description, we will sometimes use the terms assert and negate when referring to the rendering of a signal, signal flag, status bit, or similar apparatus into its logically true or logically false state, respectively, and the term toggle to indicate the logical inversion of a signal from one logical state to the other. Alternatively, we may refer to the mutually exclusive Boolean states as logic_0 and logic_1. Of course, as is well known, consistent system operation can be obtained by reversing the logic sense of all such signals, such that signals described herein as logically true become logically false and vice versa. Furthermore, it is of no relevance in such systems which specific voltage levels are selected to represent each of the logic states.

By way of example, in an ultra-wideband ("UWB") communication system, a series of special processing steps are performed by a UWB transmitter to prepare payload data for transmission via a packet-based UWB channel. Upon reception, a corresponding series of reversing steps are performed by a UWB receiver to recover the data payload. Details of both series of processing steps are fully described in IEEE Standards 802.15.4 ("802.15.4") and 802.15.4a ("802.15.4a"), copies of which are submitted herewith and which are expressly incorporated herein in their entirety by reference. As is known, these Standards describe required functions of both the transmit and receive portions of the system, but specify implementation details only of the transmit portion of the system, leaving to implementers the choice of how to implement the receive portion.

One or more of us have developed certain improvements for use in UWB communication systems, which improvements are fully described in the following pending applications or issued patents, all of which are expressly incorporated herein in their entirety:

"A Method and Apparatus for Transmitting and Receiving Convolutionally Coded Data", U.S. Pat. No. 7,636,397, issued 22 Dec. 2009;

"A Method and Apparatus for Generating Codewords", U.S. Pat. No. 7,787,544, issued 31 Jul. 2010;

"A Method and Apparatus for Transmitting and Receiving Convolutionally Coded Data", U.S. Pat. No. 8,358,709, issued 22 Jan. 2013; and "Receiver for Use in an Ultra-Wideband Communication System", U.S. Pat. No. 8,437,432, issued 7 May 2013;

"Convolution Code for Use in a Communication System", U.S. Pat. No. 8,677,224, issued 18 Mar. 2014;

"Adaptive Ternary A/D Converter for Use in an Ultra-Wideband Communication System", U.S. Pat. No. 8,436,758, issued 7 May 2013;

"Receiver for Use in an Ultra-Wideband Communication System", U.S. Pat. No. 8,760,334, issued 24 Jun. 2014;

"Receiver for Use in an Ultra-Wideband Communication System", U.S. Pat. No. 9,054,790, issued 9 Jun. 2015; and "Adaptive Ternary A/D Converter for Use in an Ultra-Wideband Communication System", U.S. Pat. No. 9,325,338, issued 26 Apr. 2016.

As is known, the 802.15.4a UWB PHY uses the following frame structure:

| Sync | SFD | PHR | DATA |
| --- | --- | --- | --- |

The vulnerabilities here are:
1) if the start of the Sync is known in advance or detected by listening to the packet, the rest of the sync is entirely predictable.
2) The Sync is periodic, i.e., it repeats the same symbol again and again, so a version which is delayed by just one symbol looks like almost identical to the original with no delay.

The code which is repeated in the Sync sequence is a so-called Ipatov code. (See earlier patents). Ipatov codes have the useful channel sounding property that they have perfect periodic auto-correlation ("PPAC"), i.e., if one of these codes is transmitted repeatedly hack to back, then correlating it with a copy of itself results in a Kronecker delta function (see, https://en.wikipedia.org/wiki/Kronecker_delta). The vulnerability identified above can be removed by changing the symbol at every symbol transition during the Sync sequence to one of the very large number of possible Ipatov codes, but this destroys the PPAC nature of these codes because they only have perfect auto-correlation if the same code is sent repeatedly back to back. However, if the code is changed each time a new symbol is sent, then the auto-correlation function has sidelobes which do not cancel out.

Let us assume that we change the code for each symbol we send. As noted above, the sidelobes no longer cancel out, but those sidelobes do change with each code change. Whereas the peak of the auto-correlation is always equal to the number of pulses in the code (9 in these earlier examples), the sidelobes are always different. This means that we can actually get a good channel estimation by sending a long enough succession of different codes. Because the sidelobes are randomly positive or negative they eventually average out to zero. The problem with doing this is that it requires a much larger number of codes such that the sums of the sidelobes will eventually get small enough so as to be negligible, and hence a much longer estimation sequence than if we had used the same Ipatov code for every symbol. However, any code with good auto-correlation properties (i.e., having a good Golay Merit Factor) will do just as well.

We submit that what is needed is an improved method and apparatus for use in the receiver of a wireless communication system to perform channel sounding. In particular, we submit that such a method and apparatus should provide performance generally comparable to the best prior art techniques, but allow asymmetric delays to be used without significantly reducing accuracy.

BRIEF SUMMARY OF THE INVENTION

In accordance with a preferred embodiment of our invention, we provide a method for use in a wireless communication system comprising a transmitter and a receiver. In one embodiment, the method comprises a first process and a second process. In this embodiment, the first process pseudo-randomly generates, as a function of a seed, a first code set of m codes. In this embodiment, the second process further comprises both transmitter functions and receiver functions. In accordance with this second process, the transmitter receives from the first process a transmitter code set comprising the first code set; and then transmits the transmitter code set. In accordance with this second process, the receiver first receives from the first process a receiver code set comprising the first code set; and then receives a channel-distorted form of the transmitter code set. The receiver then develops a set of m channel correlations by correlating each code of the receiver code set with the corresponding code of the channel-distorted form of the transmitter code set; and, finally; develops a channel estimate by accumulating the set of m channel correlations.

In one embodiment, the first process receives the seed from a seed delivery facility.

In one other embodiment, the first process pseudo-randomly generates, as a function of a seed, a first code set of m codes, wherein the first code set is substantially group complementary.

In yet another embodiment, the first process is iterative, and, in each loop, the first process first develops a set of m metric correlations by auto-correlating each of the m codes comprising the first code set; the process then develops a metric by accumulating at least a selected portion of the m metric correlations, the metric being selected to measure the degree to which the first code set is group complementary; and, finally, if the metric indicates that the first code set is not substantially group complementary, the process selectively modifies the first code set before looping.

In one other embodiment, an iterative third process is provided, wherein, in each loop, this third process first develops a set of m metric correlations by cross-correlating each of the m codes comprising the first code set with a respective one of the codes comprising the second code set; this process then develops a metric by accumulating at least a selected portion of the m metric correlations, the metric being selected to measure the degree to which the first code set is group complementary; and, finally, if the metric indicates that the first code set is not substantially group complementary, this process selectively modifies the first code set before looping.

In still another embodiment, in the second process, the transmitter is adapted to transmit at least one of the transmitted codes followed by a selected period of silence.

In one further embodiment, a wireless communication system is configured to perform our method for secure channel sounding.

The methods of our invention may be embodied in computer readable code on a suitable non-transitory computer readable medium such that when a processor executes the computer readable code, the processor executes the respective method.

The methods of our invention may be embodied in non-transitory computer readable code on a suitable computer readable medium such that when a processor executes the computer readable code, the processor executes the respective method.

BRIEF DESCRIPTION OF THE SEVERAL VIEWS OF THE DRAWINGS

Our invention may be more fully understood by a description of certain preferred embodiments in conjunction with the attached drawings in which:

FIG. 14, comprising

Figure 1:
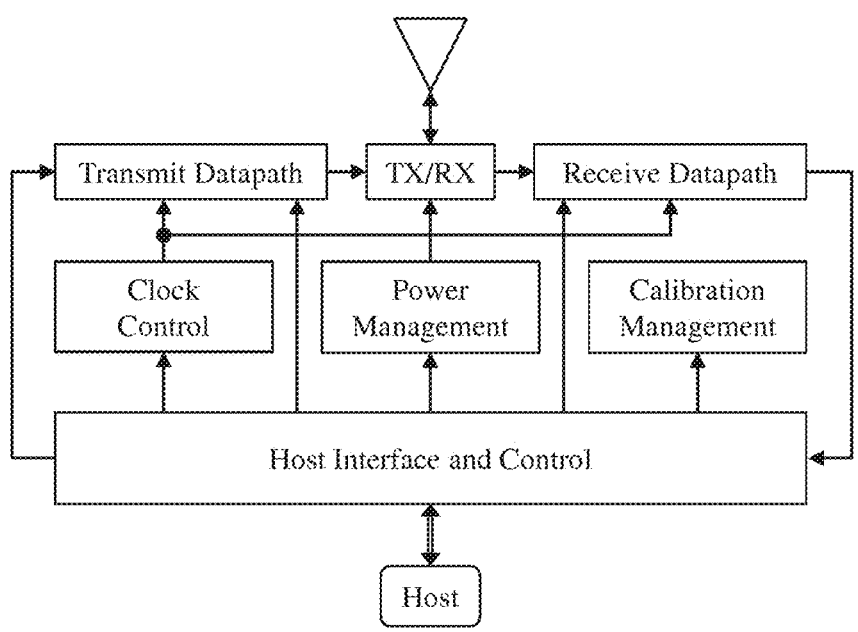
FIG. 1 illustrates, in block diagram form, one embodiment of a receiver adapted for use in a UWB communication system, the receiver comprising both transmission and reception facilities.
Figure 2:
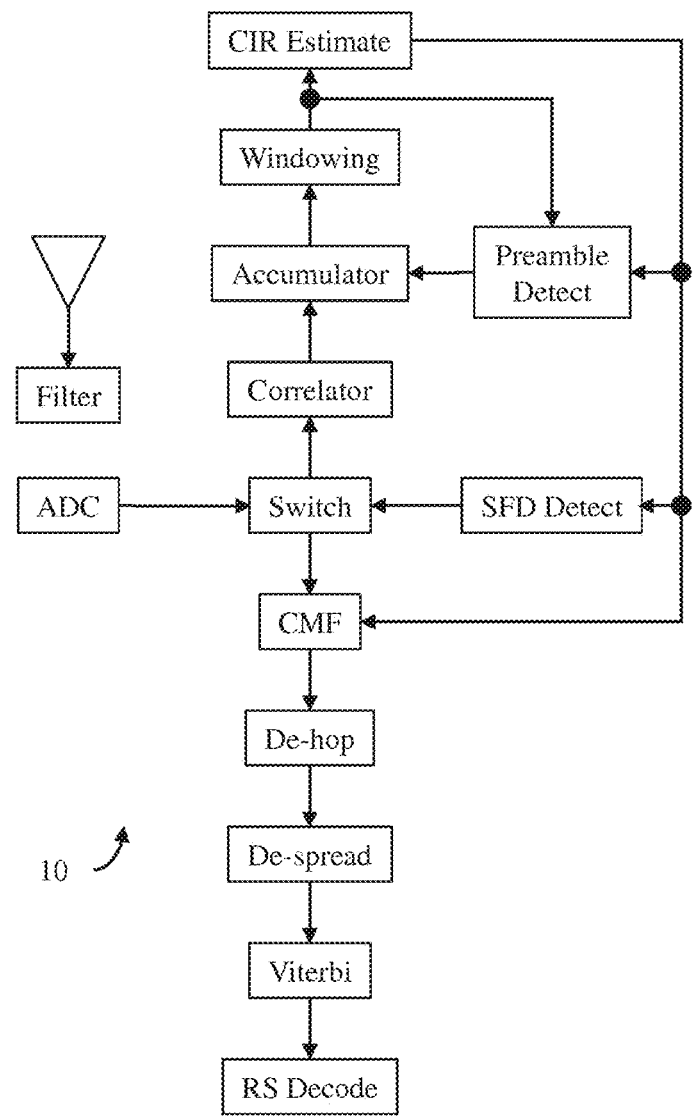
FIG. 2 illustrates, in block diagram form, one embodiment of a receiver facility adapted to practice our invention.

In the drawings, similar elements will be similarly numbered whenever possible. However, this practice is simply for convenience of reference and to avoid unnecessary proliferation of numbers, and is not intended to imply or suggest that our invention requires identity in either function or structure in the several embodiments.

DETAILED DESCRIPTION OF THE INVENTION

Figure 3:
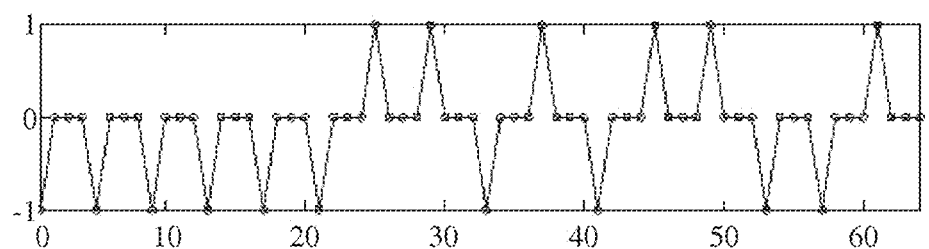
FIG. 3 illustrates, in wave diagram form, of a selected Golay Complementary Sequence ("GCS")

As is known, a GCP comprises a pair of GCSs. By way of example, consider the following zero-padded GCS (see, FIG. 3):

[$GCS_1$]-1 -1 -1 -1 -1 -1 +1 +1 -1 +1 -1 +1 -1-1 +1 and its complement (not shown):

[$\widetilde{GCS_1}$]-1 -1 ++1 -1 -1 -1 -1 -1 +1 +1 -1 +1 -1 +1 -1

Figure 4:
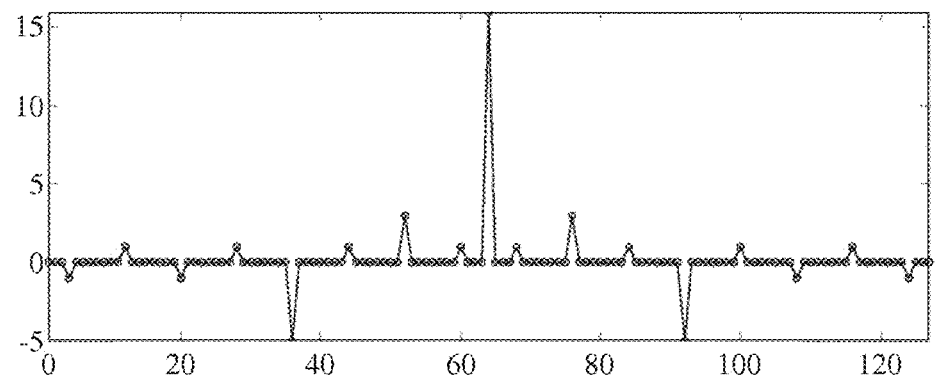
FIG. 4 illustrates, in wave diagram form, the auto-correlation of the GCS of FIG. 3.
Figure 5:
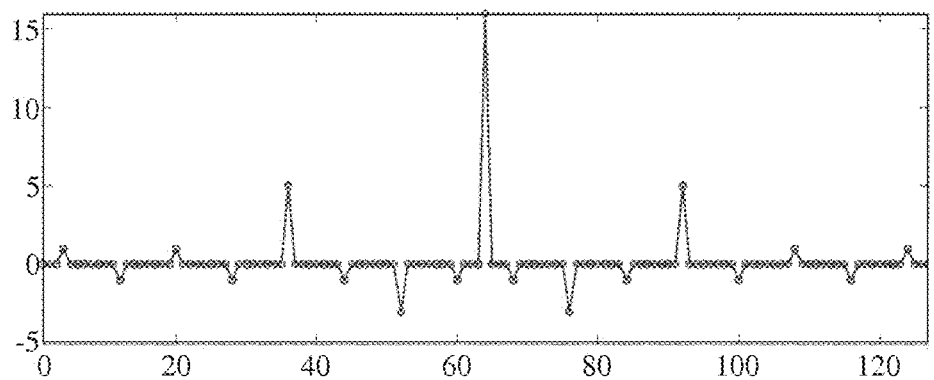
FIG. 5 illustrates, in wave diagram form, the auto-correlation of the complement of the GCS of FIG. 3.

In FIG. 4, we show the auto-correlation of $GCS_1$, and, in FIG. 5, we show the auto-correlation of $\widetilde{GCS_1}$. As can clearly be seen, the sidelobes of the auto-correlation of $GCS_1$ are exactly opposite the sidelobes of the auto-correlation of $\widetilde{GCS_1}$.

GCP Sync

In a first embodiment of our invention, we perform channel estimation using what we refer to as a CCP Synchronization ("GCP Sync") method. In accordance with this method, we transmit through the channel a pre-determined set, GCP Sync, of GCPs following the end of the normal 802.15.4a UWB PHY frame:

| Ipatov 802.15.4a Sync | SFD | PHR | DATA | GCP Sync |
|---|---|---|---|---|

In general, the GCP Sync consists of multiple pairs of GCSs. We note, however, that the two GCSs in each GCP do not necessarily have to follow each other directly. As long as both GCSs of each GCP are sent, and the receiver adds the correlation of the incoming signal with the code it expects to see at that time into its channel estimate, then the order doesn't matter. By way of example, the particular pairs that are sent may be chosen in a pseudo-random way from a large set of possible codes. Of course, to maintain synchronization, the methodology employed to develop each GCP Sync code-set must be known to both the transmitter and the receiver. Various known means may be implemented to accomplish this synchronization function in particular instantiations.

In accordance with this embodiment, we develop the identical GCP Sync code-set in both the transmitter and receiver using the synchronized methodology. Now, for purposes of explanation, let us assume that the pre-arranged synchronization function has determined that, for the first $GCR_L$, the $GCS_1$, will be transmitted first, followed some time later by the $\widetilde{GCS_1}$. In the receiver, we:

1. auto-correlate the response to the received $GCS_1$ with the internally-developed $GCS_1$;
2. auto-correlate the response to the received $\widetilde{GCS_1}$, with the internally-developed $\widetilde{GCS_1}$; and
3. sum these two correlations.

As has been demonstrated, above, this approach substantially guarantees that the auto-correlation sidelobes in our channel estimate have automatically cancelled each other out. Because of this perfect sidelobe cancellation property, the number of symbols and the length of the GCP Sync can be much shorter than if we had used either random codes or Ipatov codes.

As is known, the channel will tend to lengthen the delay spread of each transmitted code. For example, if the code was 1 microsecond long and the channel had a delay spread of 100 ns, then the energy arriving at the receiver due to one code would last for 1.1 microseconds. For this reason, a gap, i.e., a period of transmitter silence, selected to be at least equal to the expected delay spread in the channel could be inserted between one or more, and, perhaps all, of the transmitted symbols. In this way, the energy from each code symbol will arrive separately at the receiver. Of course, this will be a noisy estimate due to noise in the channel and quantisation noise in our receiver, but if we repeat this process with many different pairs of codes, we will still tend to develop a good channel estimate.

We could, of course, send the GCP Sync anywhere during the frame, including after the DATA portion, but the advantage of sending it after the SFD is that the SED acts as a timestamp which allows the receiver to know when the GCP Sync is coming, which in turn will allow the receiver to know with which code it needs to correlate the incoming signal at any one time.

For extra security we could insert pseudo-random pulses between sequences to disguise the actual codes we are using. The code length used for each symbol could vary also pseudo-randomly so that the attacker doesn't know symbol boundaries, and thus when to try to predict what code is being sent.

We note that it is possible to use much shorter symbol lengths for the GCP Sync part of the channel sounding than for the initial SYNC sequence (which uses Ipatov codes in this case). For example, consider a length 32 code with one +vc or -vc pulse every 2 ns chip. This code is only 64 ns long, but that is more than enough to accurately characterize the first path if the receiver has previously determined the path position from the Ipatov Sync. In this embodiment, path position tells the correlator which code is due at this time. Paths outside the correlator window don't correlate and are thus invisible to the receiver.

We further note that Golay originally proposed binary complementary sequences ("BCPs"). Since then other types of complementary sequences have been proposed. TCPs would work just as well. Multilevel complementary sequences have been found and would also work. Complex QAM complementary sequences have also been discovered and any of these could also be used.

CLASS

In a second embodiment, we perform channel estimation using what we refer to as a cyphered low auto-correlation sum set ("CLASS"). As in our GCP Sync approach, we append a CLASS to the end of the standard 802.15.4a frame:

| Ipatov 802.15.4a Sync | SFD | PHR | DATA | CLASS |
|---|---|---|---|---|

Figure 6:
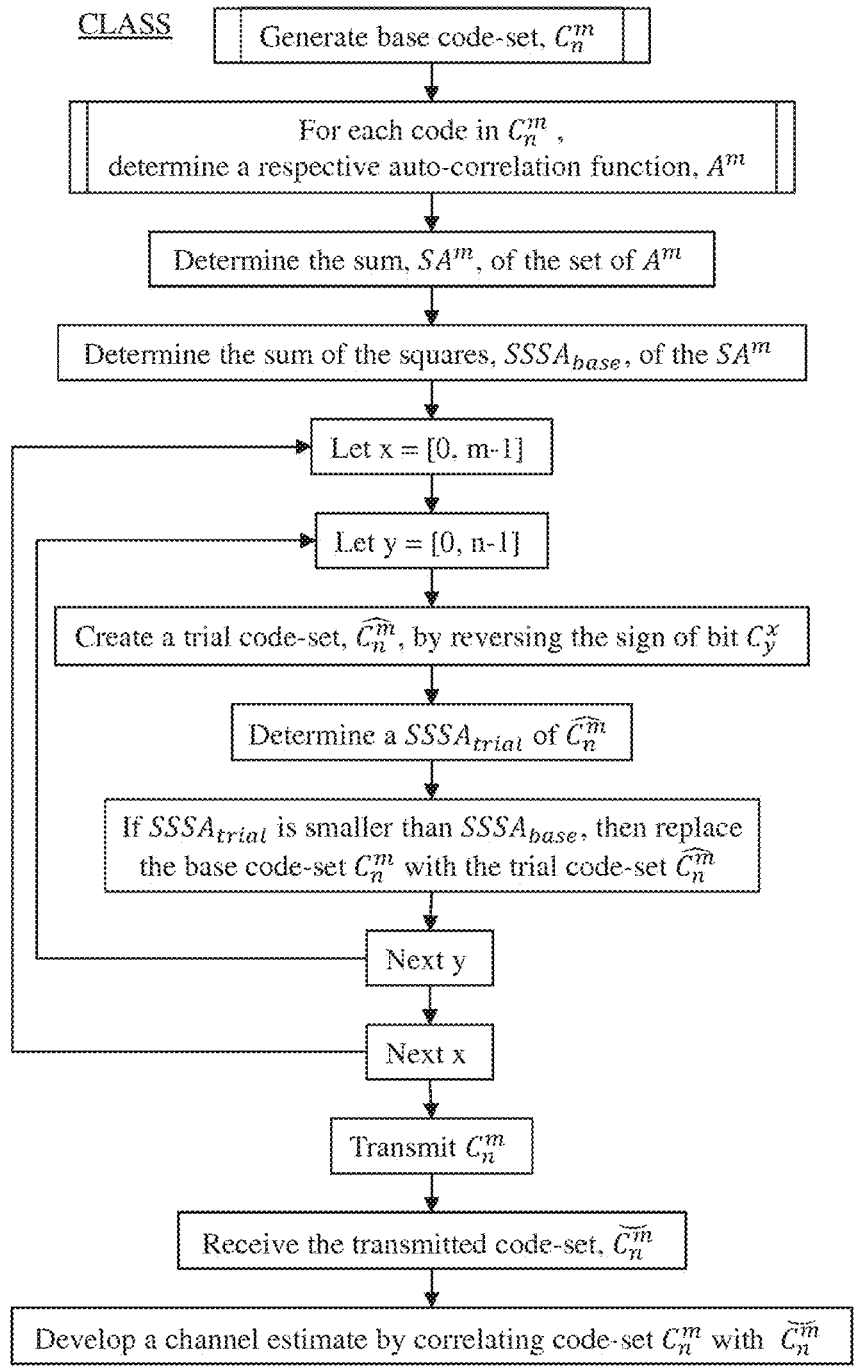
FIG. 6 illustrates, in flow diagram form, our CLASS method of channel sounding.

In accordance with this embodiment, we develop the CLASS by performing the following steps (see, FIG. 6):
in both the transmitter and the receiver:
   CLASS_1. Generate a base code-set, $C_n^m$, of m pseudo-random binary codes each having a predetermined length, n, with exactly one code for each symbol in the transmitted sequence:

CLASS_2. For each code, $C^m$, in the base code-set, determine a respective auto-correlation fiction, $A^m$;

CLASS_3. Determine the sum, $SA^m$, of the set of $A^m$;

CLASS_4. Determine the sum of the squares, $SSSA_{base}$, of the $SA^m$;

CLASS_5. Let x=[0, m−1]:

CLASS_5.1. Let y=[0, n−1]:

CLASS_5.1.1. Create a trial code-set, $\widehat{C_n^m}$, by reversing the sign of bit $C_y^x$;

CLASS_5.1.2. Determine a $SSSA_{trial}$ of $\widehat{C_n^m}$; and

CLASS_5.1.3. If $SSSA_{trial}$ is smaller than $SSSA_{base}$, then replace the base code-set $C_n^m$ with the trial code-set $\widehat{C_n^m}$;

then, in the transmitter:

CLASS_6. Transmit as the CLASS the final code-set, $C_n^m$;

and, finally, in the receiver:

CLASS_7. Receive the transmitted code $\widetilde{C_n^m}$; and

CLASS_8. Develop a channel estimate by correlating the final code-set $C_n^m$ with $\widetilde{C_n^m}$.

The final code-set, $C_n^m$, comprises the CLASS code-set that the transmitter will transmit to the receiver. Since both our transmitter and our receiver perform exactly the same process, using the same pseudo-random seed, each generates exactly the same final code-set, $C_n^m$. Thus, when the receiver correlates the received CLASS sequence with the internally-generated CLASS code-set, the resulting channel estimate exhibits relatively low sidelobe distortion. Indeed, by minimizing SSSA, our method ensures that the power in the sum of the sidelobes of the auto-correlation functions of the generated code-set is low, thereby tending to minimize sidelobe distortion.

We recognize that various modifications may be made in our CLASS method. By way of example, consider the following variations:

1. The more bits in each code that are examined, the greater the number of computations that are required. We have found that if only a subset of the bits are examined in Step 5.1 the resultant set of codes can have sufficiently low auto-correlation sidelobes, i.e., a sufficiently low SSSA. If not all bits are being examined, the bits at the starts and ends of the code have the most impact on the size of the sidelobes. This is because modification of central bits in the code does not affect the entire auto-correlation function, but only the central part of it, whereas the end bits affect the whole auto-correlation function. When we use the term "sufficiently" here, we mean to a low enough level so that a real path can be distinguished from the sidelobes. For example, you can see in FIG. 11 that the precursor sidelobes to the left have been reduced sufficiently to reveal the true first path, whereas, on the right, you can see that the postcursor sidelobes, which have not been optimised, have not been sufficiently reduced; it would thus be difficult to distinguish a first path that was 30 dBs down on the main paths.

2. If a second pass through the codes is done, i.e., Step 5 is repeated, then we have found that fewer bits need to be examined. An advantage of doing this second pass is that the fewer bits that are changed, the less predictable is the whole sequence and hence the sequence is inherently less vulnerable to attack.

3. Step 5.1.1, above, does not need to be repeated in brute force every time. There are shortcuts: for example, the auto-correlation function of each code can be stored and subtracted before adding in the auto-correlation of the changed code. Also the auto-correlation of the changed code can be developed by calculating the effect of reversing just one bit on the auto-correlation rather than re-calculating the entire auto-correlation again. We believe that this particular approach will prove particularly suitable for optimal hardware implementation.

4. When a code is being examined in Step 5.1, the SSSA of all the previous codes, up to and including this one, could be used instead of the SSSA of all of the codes. This generally results in worse overall performance for the same number of bit reversal operations. However, lost performance can be recovered if more (2 to 4x) bit reversals were used. This approach also has some advantages because the auto-correlation accumulator can use fewer bits of precision, and because the algorithm can be executed without initial latency.

5. The number of tested bit-inversions can be variable. For example, initial codes could be optimized with fewer test inversions, and only the final few codes could be executed with much higher bit inversion count. This is because intermediate sidelobe metrics generated after several codes is irrelevant. Only the final sidelobe metric, i.e., after all the codes have been processed, determines final performance. The intent here is to save processing power/time while making sure that final metric is as low as possible. It is also possible, for additional security, to leave some of the symbols unchanged at all, and only execute the sidelobe metric minimization algorithm on a subset of symbols. This approach allows some of the symbols to be completely random so that an attacker has no clues that they have been altered.

6. Another variant of our method involves not doing any bit-inversions, but instead generating a few candidate pseudo-random codes and selecting the one which best minimizes the sidelobe metric. For example for each required code, 4 code candidates could be generated. Then, 4 candidate auto-correlation functions would be added to the auto-correlation functions of other codes, and the candidate which best complements other codes, would be selected.

7. As with the GCP sync, the CLASS sequence can be sent any time after the SFD; it need not be sent only after the DATA.

8. Note the codes can be sent in any order once the code-set has been generated. For security reasons, it may be beneficial to send the codes in a different order than the order in which they were generated. So long as both the transmitter and the receiver know the ordering, they will stay in sync.

9. Per-group minimization of sidelobes could open up the possibility of an attack based on the attacker predicting certain sequences of bits (especially late bits in the last symbols). This is possible because the attacker knows that the final sidelobe metric (after most symbols have been transmitted) will be very low, and therefore could calculate bit sequences which similarly minimize the sidelobe metric of the previous symbols. Such bit sequences might be similar to the actual transmitted bits. To prevent such possibility, we might add a number of dummy symbols at selected positions within the transmitted code sequence. Such dummy symbols (which could be just random bit sequences) would not have their sidelobe metric minimized, and would be ignored by the genuine receiver. However, they would add overall sidelobes to the set of transmitted symbols. Again, so long as both the transmitter and the receiver know the ordering, they will stay in sync. However, since the attacker would not be able to distinguish between true and dummy symbols, it would have its sidelobe metric contaminated, thus preventing (or at least diminishing the likelihood of success of) this particular attack mechanism.

10. Let us again assume that, in addition to the valid symbols with which the receiver correlates, we will transmit one or more dummy symbols. Some of the valid symbols could be unmodified (purely random) and some could be modified to minimize the overall sidelobe metric of the whole set of valid symbols. In general, according to this approach, there can be multiple variants of scheduling transmissions of valid modified, valid unmodified and dummy symbols. They might be all pseudo-randomly interleaved, or sent sequentially in some order. For example: random symbols (dummy and unmodified valid ones, possibly pseudo-randomly interleaved together) might be sent first, followed by modified valid ones. Other combinations are also possible. Take, for example, an embodiment in which groups of dummy/valid codes are to be pseudo-randomly interleaved, i.e., mixed, then the existing pseudo-random code generator could be employed pseudo-randomly to generate a code index comprising a schedule according to which the valid and dummy symbols would be transmitted and received. Since both the transmitter and the receiver would be using identical code generators, then the receiver would know from the common code index which of the received codes it should consider valid, and which ones are dummy and may be ignored. Consider an embodiment in which the number of valid codes, m, is 8, and the selected number of dummy codes, k, is 4, resulting in a 12-code schedule; then, in accordance with one possible code index format, a "1" would indicate a valid code and a "0" would indicate a dummy code in the transmitted sequence of codes. Thus, a code index of "011011101101" would indicate that codes 2, 3, 5, 6, 7, 9, 10, 12 are valid, but codes 1, 4, 8, 11 are dummy. If desired, the code generator may, from time to time, change both the length and internal sequence of the code indexes; upon receipt, the transmitter and receiver can initiate use of the new code index, either immediately or after some pre-determined delay. It would also be possible for the code generator to develop and schedule multiple code indexes for use with a single code set, thereby adding further pseudo-randomness to the transmitted code sequence.

LCSSS

In a third embodiment, we perform channel estimation using what we refer to as a low cross-correlation sidelobe sum set ("LCSSS"). As in our GCP Sync and CLASS approaches, we append a LCSSS to the end of the standard 802.15.4a frame:

| Ipatov 802.15.4a Sync | SFD | PHR | DATA | LCSSS |

Figure 7:
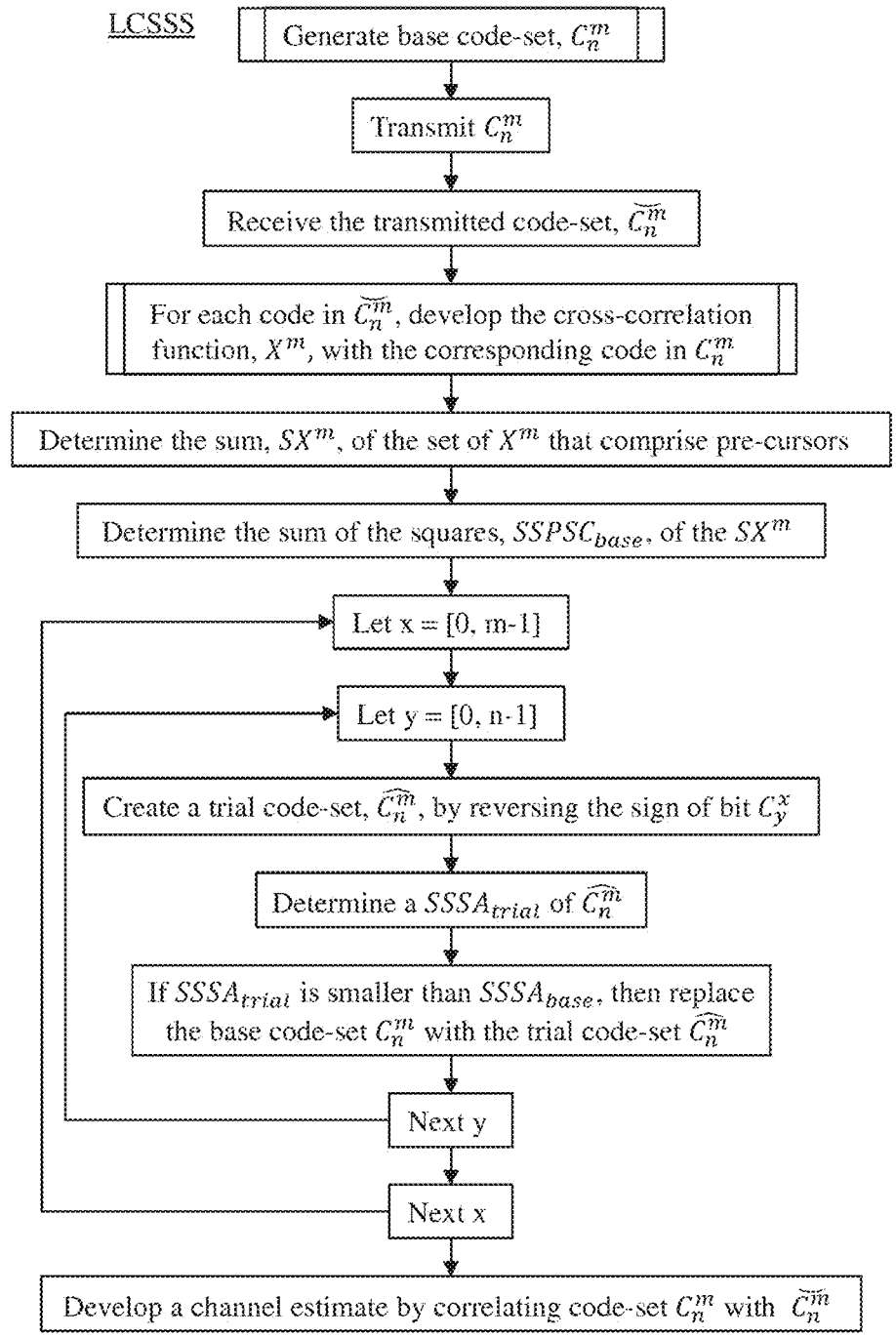
FIG. 7 illustrates, in flow diagram form, our LCSSS method of channel sounding.

In accordance with this embodiment, we develop the LCSSS by performing the following steps (see, FIG. 7):

in both the transmitter and the receiver:

LCSSS_1. Generate a base code-set, $C_n^m$, of m pseudo-random binary codes each having a predetermined length, n, with exactly one code for each symbol in the transmitted sequence;

then, in the transmitter:

LCSSS_2. Transmit as the LCSSS the base code-set, $C_n^m$;

and, finally, in the receiver:

LCSSS_3. Receive the transmitted code-set, $\widetilde{C_n^m}$;

LCSSS_4. For each code in $\widetilde{C_n^m}$, develop the cross-correlation function, $X^m$, with the corresponding code in $C_n^m$;

LCSSS_5. Determine the sum $SX^m$, of the set of $Z^m$ that comprise pre-cursors*;

(*Note: pre-cursors comprise the cross-correlation values that precede the center of the cross-correlation function.)

LCSSS_6. Determine the sum of the squares, $SSPSC_{base}$, of the $SX^m$;

LCSSS_7. Let x[0, m−1]:
  LCSSS_7.1.1. Let y=[0, n−1]:
    LCSSS_7.1.1.1. Create a trial code-set, $\widetilde{C_n^m}$, by reversing the sign of bit $C_y^x$;
    LCSSS_7.1.1.2. Determine a $SSPSC_{trial}$ of $\widetilde{C_n^m}$; and
    LCSSS_7.1.1.3. If $SSPSC_{trial}$ is smaller than $SSPSC_{base}$, then replace the base code-set $C_n^m$ with the trial code-set $\widetilde{C_n^m}$.

LCSSS_8. Develop a channel estimate by correlating the final code-set $C_n^m$ with $\widetilde{C_n^m}$.

As with our CLASS method, the resulting channel estimate exhibits relatively low sidelobe distortion. Indeed, by minimizing SSPSC, our method ensures that the power in the sum of the pre-cursors of the cross-correlation functions of the generated code-set is low, thereby tending to minimize sidelobe distortion. Using our LCSSS approach, the first path of the channel estimate can be found without the usual sidelobe distortion.

We recognize that various modifications may be made in our LCSSS method. By way of example, consider the following variations:

1. The more bits in each code that are examined, the greater the number of computations that are required. We have found that if only a subset of the bits are examined in Step 3.5.1 the resultant set of codes can have sufficiently low auto-correlation sidelobes, i.e., a sufficiently low SSSA. If not all bits are being examined, the bits at the starts and ends of the code have the most impact on the size of the sidelobes. This is because modification of central bits in the code does not affect the entire auto-correlation function, but only the central part of it, whereas the end bits affect the whole auto-correlation function.

2. If a second pass through the codes is done, i.e., Step 5 is repeated, then we have found that fewer bits need to be examined.

3. Step 3.5.1.1, above, does not need to be repeated in brute force every time. There are shortcuts: for example, the auto-correlation function of each code can be stored and subtracted before adding in the auto-correlation of the changed code. Also the auto-correlation of the changed code can be developed by calculating the effect of reversing just one hit on the auto-correlation rather than re-calculating the entire autocorrelation again. We believe that this particular approach will prove particularly suitable for optimal hardware implementation.

4. When a code is being examined in Step 3.5.1, the SSPSC of all the previous codes, up to and including this one, could be used instead of the SSPSC of all of the codes. This generally results in worse overall performance for the same number of bit reversal operations. However, lost performance can be recovered if more (2 to 4x) bit reversals were used. This approach also has some advantages because the auto-correlation accumulator can use fewer bits of precision, and because the algorithm can be executed without initial latency.

5. The number of tested bit-inversions can be variable. For example, initial codes could be optimized with fewer test inversions, and only the final few codes could be executed with much higher bit inversion count. This is because intermediate sidelobe metrics generated after several codes is irrelevant. Only the final sidelobe metric, i.e., after all the codes have been processed, determines final performance. The intent here is no save processing power/time while making sure that final metric is as low as possible.

6. As with the GCP sync, the LCSSS code-set does not need to be sent after the DATA, it can be sent any time after the SFD.

7. One theoretically possible attack approach could involve the attacker trying to predict how the receiver would change the transmitted random bits for correlation in its receiver, and then transmitting those predicted bits earlier. Such prediction attempts could be based on the analysis of sidelobes, knowing that the receiver's LCSSS algorithm would try to minimize those. Therefore, to further enhance security, the transmitter could add a number of dummy symbols to the transmission. Such dummy symbols (which could be just random bit sequences) would not be processed by the receiver LCSSS algorithm (which is complementing sidelobes of the valid symbols); instead they would be ignored. However, these dummy symbols would add additional sidelobes to the set of transmitted symbols. Since the attacker would not be able to distinguish between true and dummy symbols, the sidelobe metrics of the attacker's transmission would be contaminated, thus preventing or diminishing the possibility that the receiver's correlator will predict the correct LCSSS bits. There can be multiple variants of scheduling transmissions of valid and dummy symbols, for example, they could be all pseudo-randomly interleaved.

One advantage of the LCSSS process over the CLASS process is that the transmitted sequence is completely random with no modifications. Like the CLASS sequence, the LCSSS sequence has very low precursor sidelobes and so gives an almost distortion free first path estimate; but the CLASS sequence has the disadvantage that some or all of the transmitted codes have been modified from their original random states to make codes with low auto-correlation sidelobe sums. An attacker might be able to exploit this property of the modified code-set to guess some of the bits, and thus successfully pretend he is nearer than he actually is by transmitting these guessed bits so that they arrive earlier than the real bits.

As noted above, bit-inversion is one technique that may be effectively employed for seeking better code sequences. However, this technique will be numerically it efficient if it requires recalculation of all auto-correlations for every candidate bit-inversion. We have discovered, however, that it is possible to compute only the difference that a single bit-inversion would make to the cross-correlation. We have determined that the following exemplary pseudo-code algorithm may be implemented efficiently in hardware:

```
txCodes - generated random codes (using seed and secure cypher)
rxCodes=txCodes;
groupSize=64; % split preamble into N groups, each 64-symbols
xcSum = zeros(1,63); % sum of cross-correlations
for m=1: groupSize % sum all auto-correlations (of all initial codes)
    xcSum = xcSum+xcorr(txCodes(m), rxCodes(m));
end
for m=1: groupSize % loop for all codes in a group
TXC=txCodes(m,:);
RXC=rxCodes(m,:);
for b=1:64 % try to invert all 64 bits
    diff=[zeros(1,64-b) -sign(RXC(b))*TXC]; % diff vector
    if (-2*sum(diff *xcSum)) > (b-1) % if metric is decreased, accept
inversion
        xcSum = xcSum(1:63)+diff(1:63); % new sum of all autocorrelations
        RXC(b) = -RXC(b); % invert bit #b
    end
end
rxCodes(m) = RXC;
end
```

In the case of CLASS, where bit inversion is done in both the transmitter and the receiver, a similar approach may be employed, but the "diff" variable is formed as a sum of two vectors.

Figure 8:
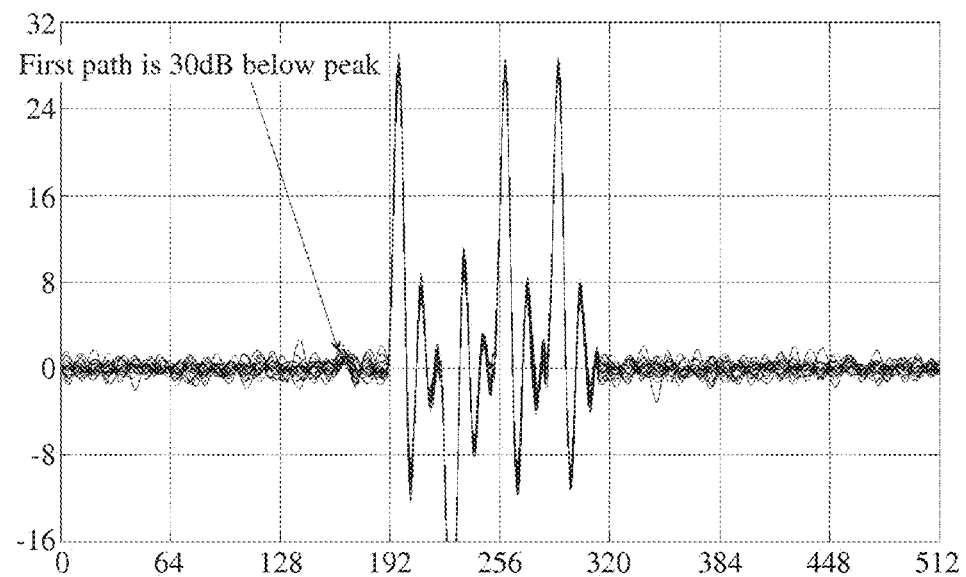
FIG. 8 illustrates, in wave diagram form, a purely random set of codes correlated with itself, wherein each code comprises 64 symbols.
Figure 9:
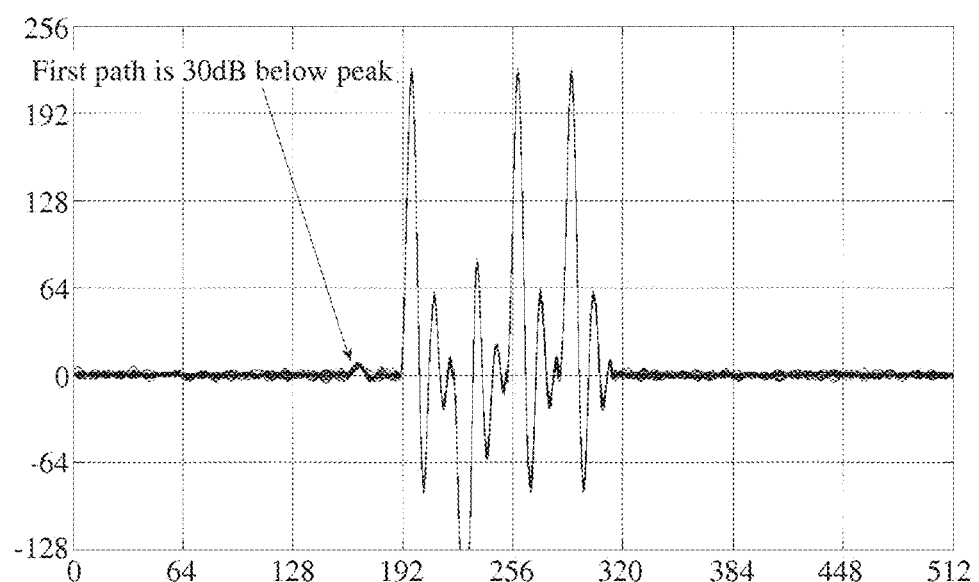
FIG. 9 illustrates, in wave diagram form, a purely random set of codes correlated with itself, wherein each code comprises 512 symbols.
Figure 10:
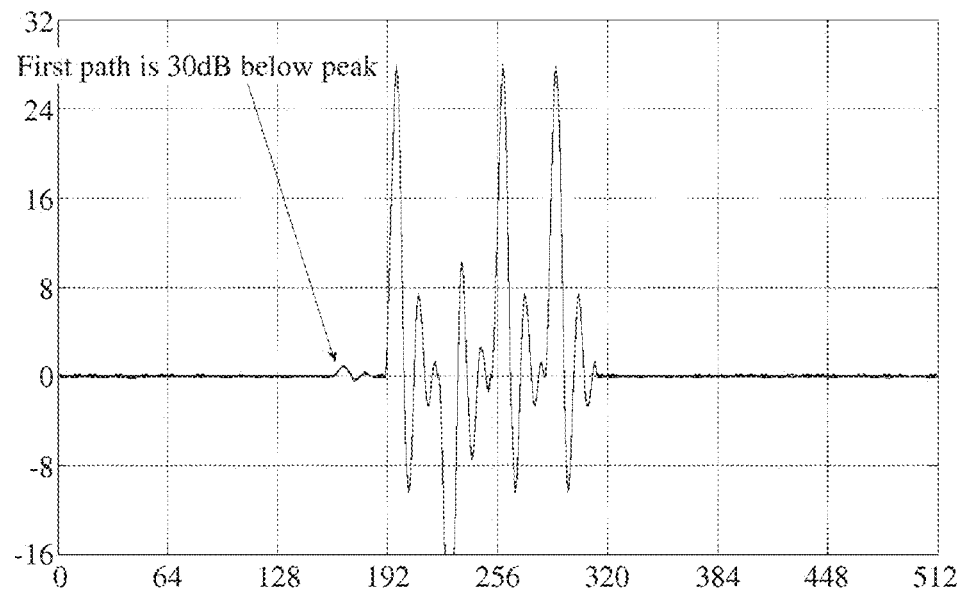
FIG. 10 illustrates, in wave diagram form, one exemplary code-set generated in accordance with our CLASS method correlated with itself, wherein each code comprises 64 symbols.
Figure 11:
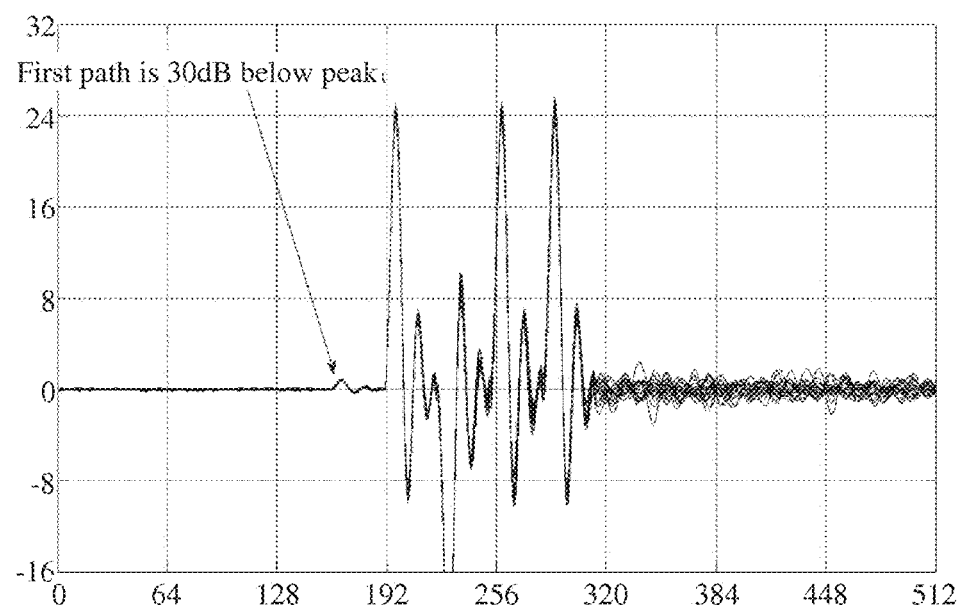
FIG. 11 illustrates, in wave diagram form, one exemplary code-set generated in accordance with our LCSSS method correlated with itself, wherein each code comprises 64 symbols.

Let us now compare the channel estimate performance of the following alternative methods:

Method 1. A purely random set of codes, each comprising 64 symbols, correlated with itself, as shown in FIG. 8;

Method 2. A purely random set of codes, each comprising 512 symbols, correlated with itself, as shown in FIG. 9;

Method 3. A CLASS set of code, each comprising 64 symbols, correlated with itself, as shown in FIG. 10; and Method 4: An LCSSS set of random codes, each comprising 64 symbols, correlated with itself, as shown in FIG. 11.

Figure 12:
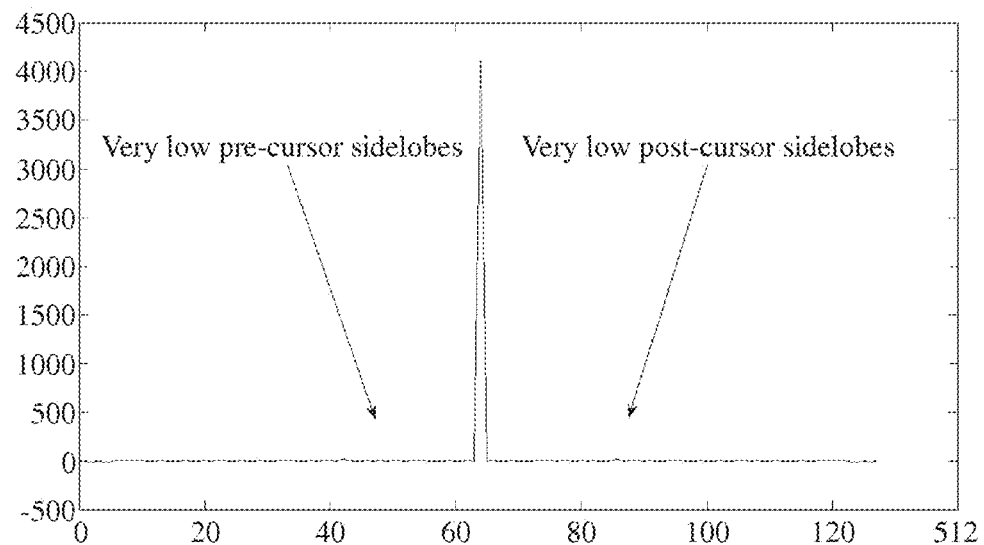
FIG. 12 illustrates, in wave diagram form, the sum of auto-correlations of the CLASS code-set used to generate the waveform illustrated in FIG. 10.
Figure 13:
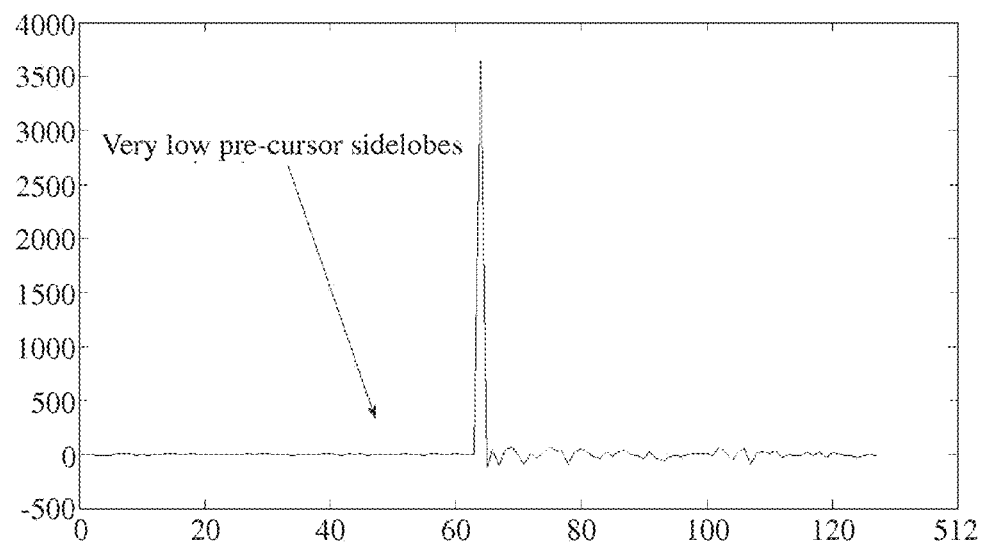
FIG. 13 illustrates, in wave diagram form, the sum of cross-correlations of the LCSSS transmit and receive code-sets used to generate the waveform illustrated in FIG. 11.

As can be seen by comparing FIG. 8 and FIG. 9 to FIG. 10 and FIG. 11, both the CLASS channel estimate (Method 4) and the LCSSS channel estimate (Method 4) are much better than the purely random channel estimates (Methods 1 and 2) despite being 8 times shorter. In FIG. 12, we have shown the sum of auto-correlation functions of the exemplary CLASS sequence; and, in FIG. 13, we have shown the sum of the cross-correlations of the LCSSS transmit and receive sets. As will be clear to those skilled in this art, these waveforms demonstrate that both our CLASS and LCSSS methods effectively cancel the sidelobes resulting from insertion of the random codes. Further, when compared to, say, the 512 codes of Method 2, both of our new methods reduce both power consumption and airtime.

Integrated CLASS and LCSSS

Figure 14A:
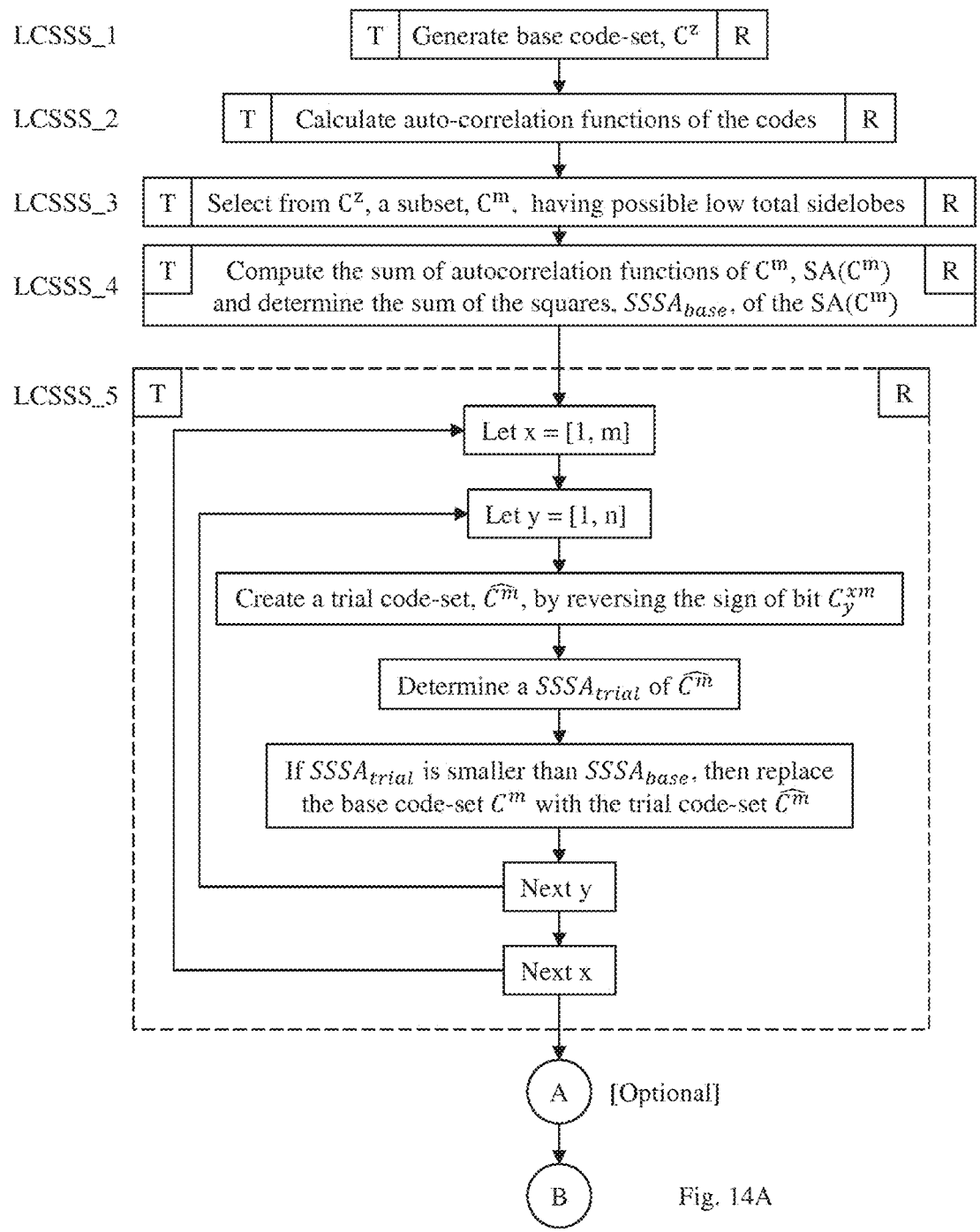
FIG. 14A, FIG. 14B and FIG. 14C, illustrates, in flow diagram form, our method for selectively generating either the CLASS or LCSSS code-sets.
Figure 14B:
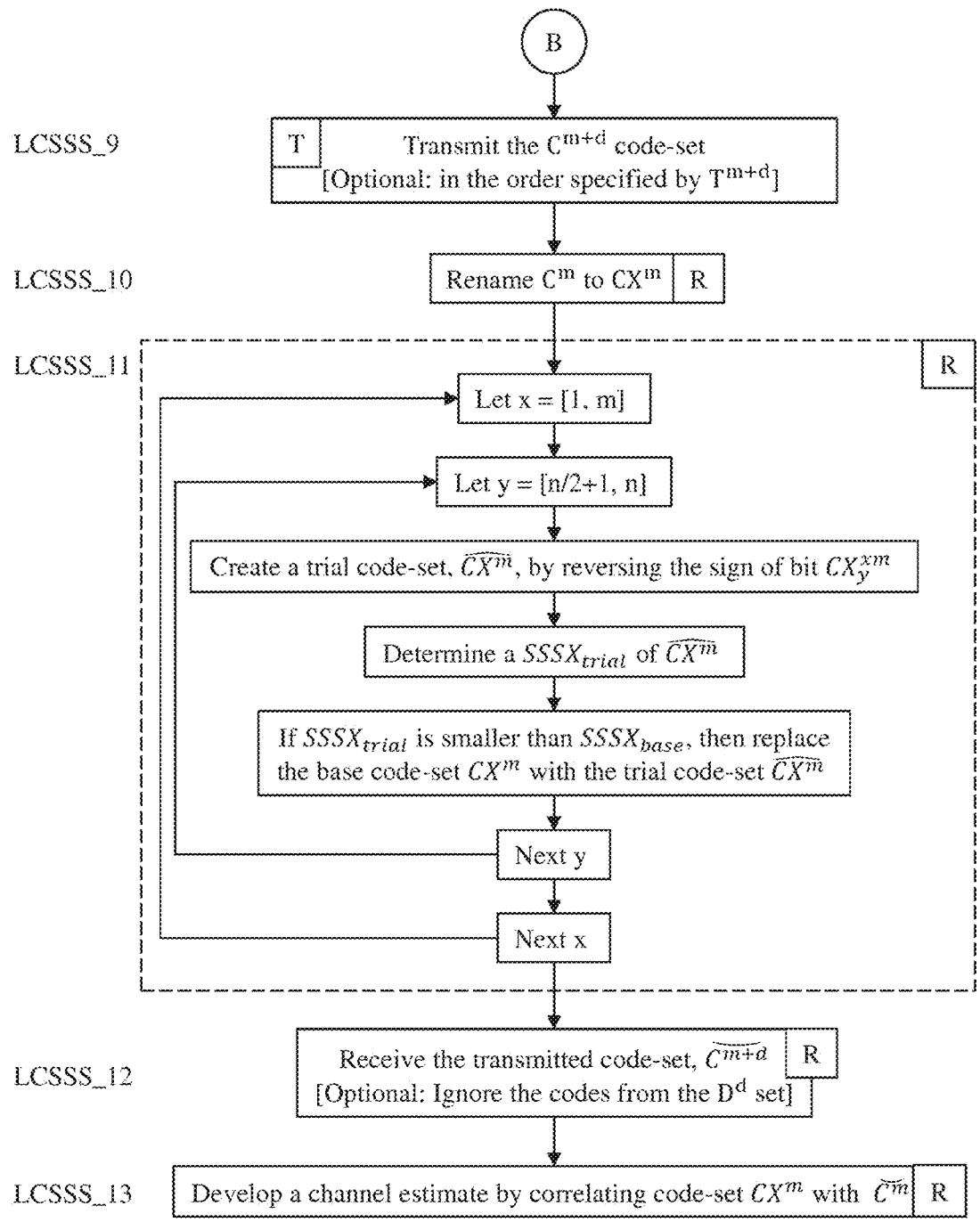
Figure 14C:
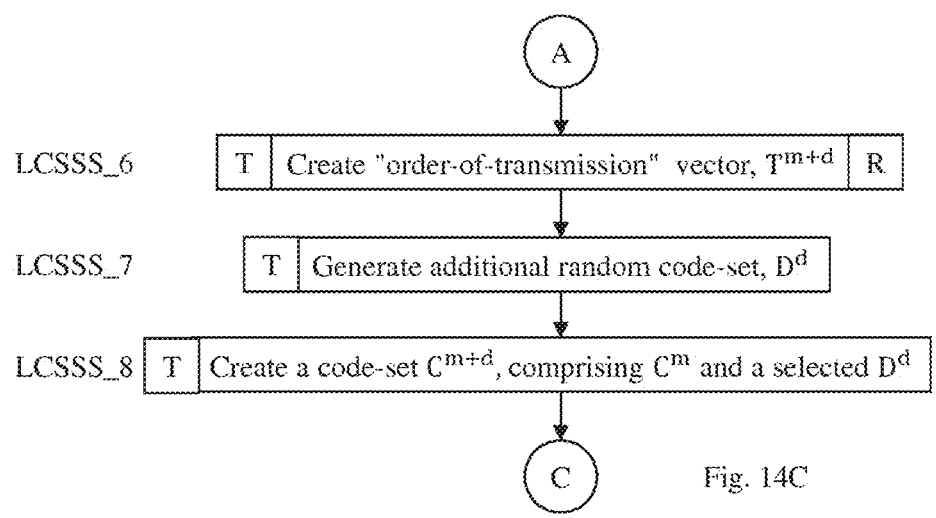

In a fourth embodiment we perform channel estimation using a single flow that selectively generates either CLASS and LCSSS. As in our CLASS and LCSSS approaches, we append the selected result to the end of the standard 802.15.4a frame. In accordance with this embodiment, we develop a selected one of the CLASS or the LCSSS by performing the following steps (see, FIG. 14):

in both transmitter and receiver:

LCSSS_1. Generate a base codeset, $C^z$ of 'z' pseudo-random binary codes each having a predetermined length, n, with exactly one code for each symbol in the transmitted sequence; let the jth bit of the ith code of $C^z$ be denoted $C_j^{iz}$;

LCSSS_2. For each code, $C^{iz}$, in the set, $C^z$, calculate its auto-correlation function of length 2n−1; let the set of these auto-correlation functions be $A(C^z)$, and let the jth value of the ith code of $A(C^z)$ be denoted $A_j(C^{iz})$;

LCSSS_3. From the larger set $C^z$ of 'z' codes, select a subset $E^m$ of 'm' codes; calculate a new function, $SA(E^m)$, whose elements are the sums of the corresponding values of the precursors in the set of auto-correlation functions, i.e., $SA_j(E^m)=\Sum_{i=1}^{m} A_j(E^{im})$;

(*Note: precursors comprise the first n−1 values of the auto/cross-correlation function.)

LCSSS_4. From many possible $E^m$ sets, select one, called $C^m$, which has a sufficiently low sum of squares of $SA(C^m)$ and call this $SSSA_{base}$, i.e., $SSSA_{base}=\Sum_{j=1}^{n-1} SA_j^2(C^m)$;

(Note: Minimizing the sum of squares minimizes the power. Another approximation to the sum of squares, e.g., sum of absolute values, could be used here. Also another metric could be minimized or maximized, e.g., peak power, sum of cubes, etc.)

(LCASS_5 comprises optional steps covering CLASS method)

LCASS_5. Let x=[1, m]:
  LCASS_5.1. Let y=[1, n]:
    LCASS_5.1.1 Create a trial code-set, $\widehat{C_n^m}$, by reversing the sign of bit y of $C_y^{xm}$;
    LCASS_5.1.2. Determine a $SSSA_{trial}$ of $\widehat{C_n^m}$ and
    LCASS_5.1.3. If $SSSA_{trial}$ is smaller than $SSSA_{base}$, then replace the base code-set $C^m$, with the trial code-set $\widehat{C_n^m}$; update $SSSA_{base}$;

LCSS_6. (optional) The total number of transmitted codes will be (m+d), where 'd' are a predetermined number of additional codes, ignored by the receiver; create a vector specifying order of (m+d) codes transmission, $T^{m+d}$, where $T^{m+d}$ may be either consecutive order 1, 2, . . . , (m+d) or random permutation of the integers from 1 to (m+d);

then, in the transmitter:

LCSSS_7. (optional) Generate a set of additional codes, $D^d$, of 'd' pseud; random binary codes, each having a predetermined length, n, with exactly one code for each symbol in the transmitted sequence;

LCSSS_8. (optional) Using additional code-sets, $D^d$, form an updated base code-set $C^{m+d}$ comprising 'm' previously generated codes and the 'd' new random codes;

LCSSS_9. Transmit the base code-set, $C^{m+d}$ in specific order using $T^{m+d}$ as indexes to select the code transmission order;

and, finally, in the receiver:

LCSSS_10. Having already determined the sum $SSSA_{base}$ (in LCSSS_4), rename it to $SSSX_{base}$, and rename $C^m$ to $CX^m$;

LCSSS_11 (optional). Let x=[1, m]:
  LCSSS_11.1. Let y=[n/2+1, n]:
    LCSSS_11.1.1. Create a trial code-set, $\widehat{CX_n^m}$, by reversing the sign of bit y of $CX_y^{xm}$;
    LCSSS_11.1.2. Determine a $SSSX_{trial}$ of $\widehat{CX_n^m}$; and
    LCSSS_11.1.3. If $SSSX_{trial}$ is smaller than $SSSX_{base}$, then replace the base code-set $CX^m$ with the trial code-set $\widehat{CX_n^m}$; and replace $SSSZ_{base}$ with $SSSX_{trial}$;

LCSSS_12, Receive an estimate of the transmitted code-set, $\widehat{C^{m+d}}$; knowing transmission code order $T^{m+d}$, identify which code is currently going to be received. If it's going to be one of the valid m codes, then program the receiver correlator with appropriate $CX^m$ code, otherwise ignore one of the d random codes belonging to the $D^d$ code-set; and LCSSS_13. Develop a channel estimate by correlating the code-set $CX^m$ with $\widehat{C_n^m}$.

In a fifth embodiment, we perform channel estimation using a parallel flow comprising a code generation process and a channel sounding process. In accordance with our code generation process, we selectively instantiate an identical pattern generation facility in both the transmitter and receiver. Each of these facilities is selectively adapted to receive a seed; and to generate, as a function of the seed, a base codeset, $C^z$, of z pseudo-random codes, each of length ii bits, wherein $C_j^{iz}$ comprises the jth bit of the ith code of $C^z$. In the field, a mechanism is provided to coordinate the transmitter and the receiver so that an identical seed is provided to the respective code generation facility, thus assuring that the identical sequence of codes is generated in both the transmitter and the receiver. For example, the transmitter may be adapted to develop the seed and thereafter to transmit that seed to the receiver using a conventional packet transaction. Alternatively, a central control facility (not shown) may be adapted to transfer the seed to both the transmitter and the receiver using know transfer mechanisms.

In accordance with the channel sounding process in this fifth embodiment:

in both transmitter and receiver:

selectively provide the seed to the respective code generation facility, each seed having the same selected value, and receive from the code generation facility the generated base codeset, $C^z$;

for each of the $C^{iz}$ in the received base codeset $C^z$, calculate a respective auto-correlation function, A, of length 2n−1, wherein $X(C^z, C^z)$ comprises the set of cross-correlation functions, and $X_j(C^{iz}, C^{iz})$ comprises the jth value of the ith code of $A(C^z)$;

from the set $C^z$ of z codes, select a subset $E^m$ of m codes, and calculate a function $SX(E^m, E^m)$, each element of which comprises the sums of the corresponding values of a selected set of precursors in the set of cross-correlation functions as determined in accordance with a function:

$$SX_j(E^m)=\Sum_{i=1}^{m} A_j(E^{im}, E^{im})$$

from a selected plurality of $E^m$, sets, select a base code set, $C^m$, which has a sufficiently tow sum of squares of $SX(C^m, C^m)$ as determined in accordance with a function:

$$SSSX_{base}=\Sum_{j=1}^{n-1} SX_j^2(C^m, C^m);$$

in only the transmitter:
transmit the base code-set; and
in only the receiver:
copy $C^m$ to $CX^m$;

let x=[1, m]:
  let y=[n/2−1, n]:
    create a trial code-set, $\widetilde{CX^m}$, by reversing a sign of bit y of $CX_y^{xm}$; determine a $SSSX_{trial}$ of $\widetilde{CX^m}$ in accordance with a function:

$SSSX_{trial}=\Sigma_{j=1}^{n-1}SX_j^2(C^m, \widetilde{CX^m}$; and if $SSSX_{trial}$ is smaller than $SSSX_{base}$, then replace the base code-set $CX^m$ with the trial code-set $\widetilde{CX^m}$ and replace $SSSX_{base}$ with $SSSX_{trial}$; and receive an estimate of the transmitted code-set. $\widehat{C_n^m}$;
develop a channel estimate by correlating the code-set $CX^m$ with $\widehat{C_n^m}$.

In a sixth embodiment, we again perform channel estimation using a parallel flow comprising a code generation process and a channel sounding process. In this embodiment we provide a code generation process substantially the same as in our fifth embodiment.

In accordance with the channel sounding process in this sixth embodiment:
in both transmitter and receiver:
selectively provide the seed to the respective code generation facility, each seed having the same selected value, and receive from the code generation facility the generated base codeset, $C^z$;
for each of the $C^{iz}$ in the received base codeset $C^z$, calculate a respective auto-correlation function, A, of length 2n−1, wherein $A(C^z)$ comprises the set of auto-correlation functions, and $A_j(C^{iz})$ comprises the jth value of the ith code of $A (C^z)$;
from the set $C^z$ of z codes, select a subset $E^m$ of m codes, and calculate a function, $SA(E^m)$, each element of which comprises the sums of the corresponding values of a selected set of precursors in the set of auto-correlation functions as determined in accordance with a function:

$SA_j(E^m)=\Sigma_{i=1}^m A_j(E_{im})$;

from a selected plurality of $E^m$ sets, select a base code set, $C^m$, which has a sufficiently low sum of squares of $SA(C^m)$ as determined in accordance with a function:

$SSSSA_{base}=\Sigma_{j=1}^{n-1}SA_j^2(C^m)$;

rename $SSSA_{base}$ as $SSSX_{base}$, and renaming $C^m$ to $CX^m$;
let x=[1, m]:
  let y=[n/2+1, n]:
    create a trial code-set, $\widetilde{CX^m}$ by reversing a sign of bit y of $CX_y^{x,m}$;
    determine a $SSSX_{trial}$ of $\widetilde{CX^m}$; and
    if $SSSX_{trial}$ is smaller than $SSSX_{base}$, then replace the base code-set $CX^m$ with the trial code-set $\widetilde{CX^m}$, and replace $SSSX_{base}$ with $SSSX_{trial}$;
in only the transmitter:
transmit the code-set, $CX^m$; and
in only the receiver:
receive an estimate of the transmitted code-set, $\widetilde{CX^m}$ and
develop a channel estimate by correlating the code-set $CX^m$ with $\widetilde{CX^m}$.

Generic Channel Sounding Flow

Figure 15:
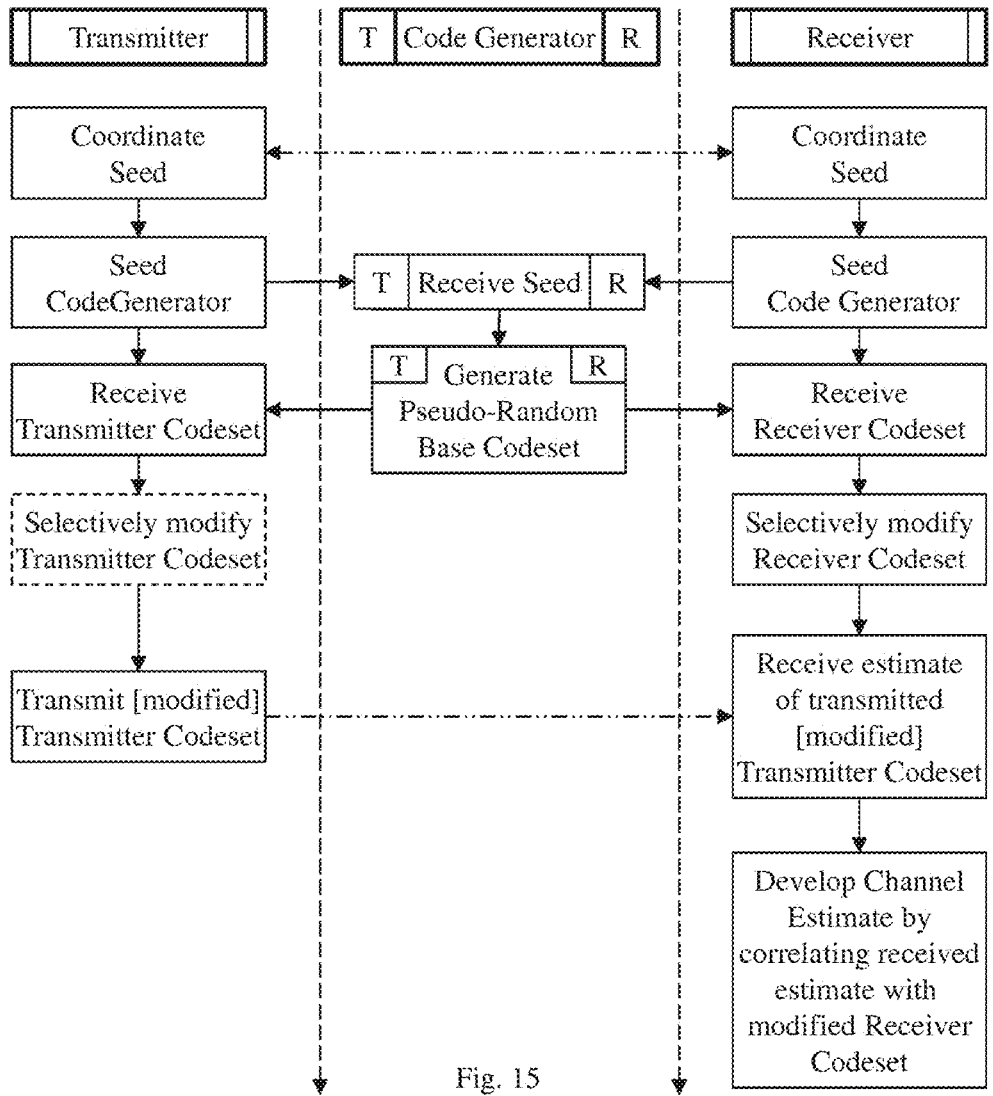
FIG. 15 illustrates, in flow diagram form, the general flow of our several methods for channel sounding.

As will be recognized by those skilled in this art, several of the flows set forth above comprise respective species of the more generic flow illustrated in FIG. 15. Viewed from this fundamental perspective, each of our channel sounding embodiments provides a generic code generation process substantially the same as in our fifth embodiment, above, and a specific channel sounding process. In accordance with each of the several channel sounding processes, both the transmitter and the receiver selectively provide the seed to the respective code generation facility, each seed having the same selected value, and receive from the code generation facility respective transmitter and receiver copies of the generated base codeset. Although there are a number of known, prior art pseudo-random code generation facilities available, we prefer to use one of the cryptographically secure pseudo-random generator facilities described in, e.g., the Federal Information Processing Standard Publication FIPS Pub 186-4, or the National Institute of Standards and Technology Special Publication NISI SP 800-90A Rev. 1. As illustrated in FIG. 15, the pseudo-random code generation process can be implemented as identical instances in both the transmitter and the receiver; or, alternatively, as a single shared instance accessible by both the transmitter and the receiver.

In accordance with the channel sounding processes described above, the transmitter is adapted to transmit the transmitter codeset received from the code generation facility. In some of our channel sounding processes, the transmitter is optionally adapted selectively to modify the transmitter codeset before transmission.

In accordance with the channel sounding processes described above, the receiver is adapted selectively to modify the receiver codeset received from the code generation facility. Then, the respective receiver receives a channel-distorted form of the transmitter codeset, which, for convenience, we shall hereinafter refer to as an "estimate". Finally, the receiver develops a channel estimate by correlating the received estimate with the receiver-modified base codeset. In those embodiments in which the transmitter transmits a transmitter-modified base codeset, the receiver develops the channel estimate by correlating the received estimate of the transmitter-modified base codeset with the receiver-modified base codeset.

Rather than minimizing sidelobes interference using transmitter/receiver correlator sequence changes, we have discovered that it is possible to use only post-processing in the receiver. In this approach, both the transmitter and the receiver would receive identical, pseudo-random sequences from the code generator. Typically, this will result in significant sidelobes. However, we note that the receiver can directly calculate these sidelobes by accumulating auto-correlations of all of the transmitted code symbols. As is known, each energy (for example coming from a strong path) will not only cause a peak in the accumulator, but also produce mini-peaks, exactly in the locations predicted by sidelobes. Therefore, it is possible to select and process the channel response samples, starting with the largest, and then iteratively subtract the sidelobe interference caused by each sample. As will be recognized, proper scaling and spreading in time needs to be taken into account in this process. In general, as more samples are processed, the sidelobes gradually decrease. Usually, with more multi-path present, it will be necessary to process more samples. However, mutual cross-interference could reduce final quality because even large samples will have their amplitudes affected by interference from other samples and paths. It would be possible, however, to perform multiple processing passes, each time also subtracting estimated interference components.

In one other interesting embodiment, let us first assume that a sequence A of m codes comprises the concatenation of two code sub-sequences: $A_1$ of n codes; and $A_2$ of (m-n) codes; i.e., $A=[A_1::A_1]$ where the symbol "::" represents the concatenation operation. Let us also assume that we are interested in the correlation between the sequence A and a different, selected sequence B. To determine this correlation, we first calculate a first correlation between B and $[A_1::0]$, where the zero indicates masking the sub-sequence $A_2$. We then calculate a second correlation between B and $[0::A_2]$, where the zero now indicates masking the sub-sequence $A_1$. If we now accumulate the two correlations, the spurious sidelobes of the first correlation will be cancelled out by the sidelobes of the second correlation. Thus, if a selected code sequence is partitioned into two or more sub-sequences, each of which is transmitted separately, we believe this approach will be effective to prevent an attacker or eavesdropper from guessing which code sequence is being used.

Binary Codes vs. Ternary Codes

In some embodiments, if a binary code is received in the receiver and then a much stronger echo of that binary code is received on top of it a few nanoseconds later, the receiver only sees the second binary code. In effect, the strong echo floods/overloads the receiver, and you cannot detect the small perturbations caused by the earlier, weaker signal. One possible solution is to use a ternary code. So, for example, instead of transmitting this binary code:
+++−+−++−−−++++−−−+−+++−−+−++−−−+++++−−
−+−+++−−+−++−−−++++−−−+−
you send, for example, this tertiary code:
+00+0+−00−+0−000+00+−−0−0+0+0+0+000+−−00−+
000−+00++000−−+−+0
This allows the smaller signal to be detected in the gaps of the powerful signal.

We have found that for a length 64 code, using a ternary code with only 16 positive or negative pulses and with zeros in the other positions works very well.
Further, the ternary code can then be sent with twice the amplitude (i.e., with 4 times the instantaneous power) as the length 64 code so that we don't lose any signal-to-noise ratio.

We have found that some code pulse grids are better than others for avoiding pulse collisions between the first path and its echo. By code pulse grid, we mean a template that defines where pulses should be present and where they should be absent.

Although we have described our invention in the context of particular embodiments, one of ordinary skill in this art will readily realize that many modifications may be made in such embodiments to adapt either to specific implementations. By way of example, it will take but little effort to adapt our invention for use with different communication schemes. Further, the several elements described above may be implemented using any of the various known semiconductor manufacturing methodologies, and, in general, be adapted so as to be operable under either hardware or software control or some combination thereof, as is known in this art. Alternatively the several methods of our invention as disclosed herein in the context of special purpose receiver apparatus may be embodied in computer readable code on a suitable non-transitory computer readable medium such that when a general or special purpose computer processor executes the computer readable code, the processor executes the respective method.

Thus it is apparent that we have provided several improved methods and apparatus for use in the transceiver of a wireless communication system to perform channel sounding. Although we have so far disclosed our invention only in the context of a packet-based UWB communication system, we appreciate that our invention is broadly applicable to other types of wireless communication systems, whether packed-based or otherwise, that perform channel sounding. Further, we submit that our invention provides performance generally comparable to the best prior art techniques but more efficiently than known implementations of such prior art techniques.

The invention claimed is:

1. A method for use in a wireless communication system comprising a transmitter, T, and a receiver, R, the method comprising:
   [1.1] a first process comprising the step of:
      [1.1.1] in a selected one of T and R:
         [1.1.1.1] pseudo-randomly generating, as a function of a seed, a first code set of m codes, where m is an integer greater than 1; and
   [1.2] a second process comprising the steps of:
      [1.2.1] in T:
         [1.2.1.1] receiving from the first process a transmitter code set comprising the first code set;
         [1.2.1.2] transmitting the transmitter code set; and
      [1.2.2] in R:
         [1.2.2.1] receiving from the first process a receiver code set comprising the first code set;
         [1.2.2.2] receiving a channel-distorted form of the transmitter code set;
         [1.2.2.3] developing a set of m channel correlations by correlating each code of the receiver code set with the corresponding code of the channel-distorted form of the transmitter code set; and
         [1.2.2.4] developing a channel estimate by accumulating the set of m channel correlations.

2. The method of claim 1, further comprising the step of:
   [1.1.0] receiving the seed via a seed delivery facility.

3. The method of claim 1, wherein step [1.1.1] is further characterized as:
   [1.1.1] pseudo-randomly generating, as a function of a seed, a first code set of m codes, wherein the first code set is substantially group complementary.

4. The method of claim 1, wherein step [1.1.1] is further characterized as:
   [1.1.1] pseudo-randomly generating, as a function of a seed, a first code set of m codes, wherein m comprises n pairs of codes, each pair comprising a Golay pair.

5. The method of claim 1, wherein step [1.1.1] is further characterized as:
   [1.1.1] pseudo-randomly generating, as a function of a seed, a first code set of m codes, wherein the first code set has sufficiently low magnitude autocorrelation sidelobes.

6. The method of claim 1, wherein step [1.1] further comprises:
   [1.1.2] developing a set of m metric correlations by auto-correlating each of them codes comprising the first code set;
   [1.1.3] developing a metric by accumulating at least a selected portion of them metric correlations, the metric being selected to measure the degree to which the first code set is group complementary;
   [1.1.4] if the metric indicates that the first code set is not substantially group complementary, selectively modifying the first code set; and
   [1.1.5] repeating steps [1.1.2] through [1.1.4].

7. The method of claim 6, wherein, in step [1.1.4], the first code set is selectively modified by replacing at least one of the m codes with a new pseudo-randomly generated code.

8. The method of claim 6, wherein, in step [1.1.4], the first code set is selectively modified by selectively inverting at least a selected one of the bits comprising at least a selected one of the m codes.

9. The method of claim 1, further comprising:
[1.3] a third process comprising the steps of:
　[1.3.1] in a selected one of T and R:
　　[1.3.1.1] developing a second code set comprising each of the m codes comprising the first code set;
　　[1.3.1.2] developing a set of m metric correlations by correlating each of them codes comprising the first code set with a respective one of the codes comprising the second code set;
　　[1.3.1.3] developing a metric by accumulating at least a selected portion of the m metric correlations, the metric being selected to measure the degree to which the first code set and the second code set are group complementary;
　　[1.3.1.4] if the metric indicates that the first code set and the second code set are not substantially group complementary, selectively modifying the second code set; and
　　[1.3.1.5] repeating steps [1.3.2] through [1.3.4];
wherein step [1.2.1.1] is further characterized as:
　[1.2.1.1] receiving from a selected one of the first and third processes a transmitter code set comprising a respective one of the first code set and the second code set; and
wherein step [1.2.2.1] is further characterized as:
　[1.2.2.1] receiving from a selected one of the first and third processes a receiver code set comprising a respective one of the first code set and the second code set.

10. The method of claim 1, further comprising:
[1.3] a third process comprising the steps of:
　[1.3.1] in a selected one of T and R:
　　[1.3.1.1] developing a second code set comprising each of the m codes comprising the first code set;
　　[1.3.1.2] developing a set of m metric correlations, each correlation obtained by correlating a first vector consisting of all the bits from one of the m codes, comprising the first code set, concatenated with a selected number of bits from the code transmitted immediately before this code, with a second vector consisting of the respective one of the codes comprising the second code set;
　　[1.3.1.3] developing a metric by accumulating at least a selected portion of the m metric correlations, the metric being selected to measure the degree to which the first code set and the second code set are group complementary;
　　[1.3.1.4] if the metric indicates that the first code set and the second code set are not substantially group complementary, selectively modifying the second code set; and
　　[1.3.1.5] repeating steps [1.3.2] through [1.3.4];
wherein step [1.2.1.1] is further characterized as:
　[1.2.1.1] receiving from a selected one of the first and third processes a transmitter code set comprising a respective one of the first code set and the second code set; and
wherein step [1.2.2.1] is further characterized as:
　[1.2.2.1] receiving from a selected one of the first and third processes a receiver code set comprising a respective one of the first code set and the second code set.

11. The method of claim 9, wherein, in step [1.3.4], the second code set is selectively modified by replacing at least one of the m codes with a new pseudo-randomly generated code.

12. The method of claim 9, wherein, in step [1.3.4], the second code set is selectively modified by selectively inverting at least a selected one of the bits comprising at least one of the m codes.

13. The method of claim 1, wherein step [1.2.1.2] is further characterized as:
　[1.2.1.2] transmitting the transmitter code set, wherein at least one of the transmitted codes is followed by a selected period of silence.

14. The method of claim 1, wherein step [1.1.1] is further characterized as:
　[1.1.1] pseudo-randomly generating, as a function of a seed, a first code set comprising m codes and k dummy codes; and
wherein step [1.2.2.3] is further characterized as:
　[1.2.2.3] developing a set of m channel correlations by correlating each of the m codes of the receiver code set with the corresponding m code of the channel-distorted form of the transmitter code set.

15. A wireless communication system configured to perform the method of claim 1.

16. A non-transitory computer readable medium including executable instructions which, when executed in a processing system, causes the processing system to perform the steps of a method according to claim 1.

* * * * *